United States Patent [19]
Discko, Jr.

[11] Patent Number: 6,116,414
[45] Date of Patent: *Sep. 12, 2000

[54] SINGLE PATIENT DOSE MEDICAMENT DISPENSER WITH APPLICATOR

[75] Inventor: John J. Discko, Jr., Hamden, Conn.

[73] Assignee: Centrix, Inc., Shelton, Conn.

[*] Notice: This patent is subject to a terminal disclaimer.

[21] Appl. No.: 09/342,756

[22] Filed: Jun. 29, 1999

Related U.S. Application Data

[60] Division of application No. 08/680,136, Jul. 15, 1996, Pat. No. 5,954,996, which is a continuation-in-part of application No. 08/275,003, Jul. 13, 1994, Pat. No. 5,660,273.

[51] Int. Cl.$^7$ ...................................... B65D 69/00
[52] U.S. Cl. ............................. 206/229; 206/209
[58] Field of Search .................. 206/15.3, 209, 206/209.1, 229, 230, 361, 362.3, 564, 570

[56] References Cited

U.S. PATENT DOCUMENTS

| | | |
|---|---|---|
| 3,618,751 | 11/1971 | Rich . |
| 3,759,375 | 9/1973 | Nappi ........................................ 206/361 |
| 3,835,834 | 9/1974 | Brown et al. ............................ 206/229 |
| 4,746,614 | 5/1988 | Devaney, Jr. et al. .................. 206/564 |
| 4,786,534 | 11/1988 | Aiken ........................................ 206/229 |
| 4,838,851 | 6/1989 | Shabo ........................................ 604/1 |
| 4,880,111 | 11/1989 | Bagwell et al. . |
| 4,880,311 | 11/1989 | Bagwell et al. ....................... 206/209.1 |
| 4,889,228 | 12/1989 | Gueret ...................................... 206/229 |
| 5,001,803 | 3/1991 | Discko, Jr. . |
| 5,106,297 | 4/1992 | Discko, Jr. . |
| 5,112,152 | 5/1992 | McBride .................................. 206/229 |
| 5,184,710 | 2/1993 | Gordon . |
| 5,184,719 | 2/1993 | Gordon ................................. 206/209.1 |
| 5,240,415 | 8/1993 | Haynie . |

*Primary Examiner*—David T. Fidei
*Attorney, Agent, or Firm*—Fattibene & Fattibene; Arthur T. Fattibene; Paul A. Fattibene

[57] ABSTRACT

A tray having wells or depressions therein for holding a medicament or material and an applicator for applying the medicament or material. The applicator well has one open end from which a portion of the applicator extends. A cover seals the medicament or material well and the applicator well and a portion of the applicator. In one embodiment, the cover is a thin sheet or film that adheres or is heat sealed to substantially the entire surface of the tray. The portion of the applicator extending beyond the applicator well is used to facilitate the removal of the cover whereby the extended portion of the applicator acts as a lever to pry the cover form the body of the tray. Additionally, packaging material required to form the tray can be substantially lessened in those cases where the applicator that is relatively large in comparison with the amount of material to be packaged. Therefore, a larger applicator that is easy to use is associated with the material without unnecessary packaging. The dispenser or package permits small quantities of material to be easily dispensed for a single use or a single patient dose. Retaining means are provided for securing the applicator by friction fit within the applicator well. In another embodiment, a hinged cover is used in combination with a tray having multiple material wells which may be jointed or separately opened and closed.

11 Claims, 10 Drawing Sheets

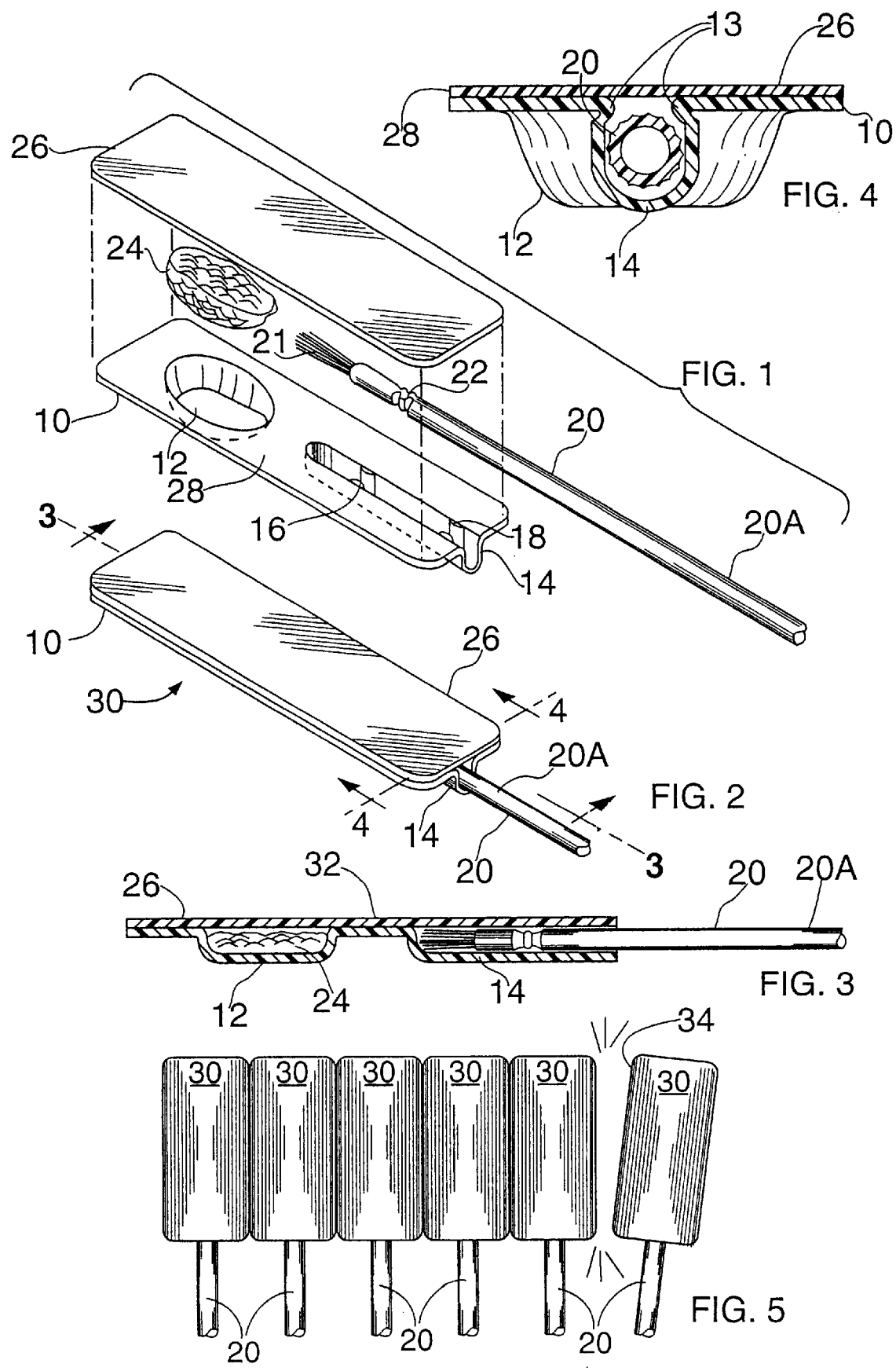

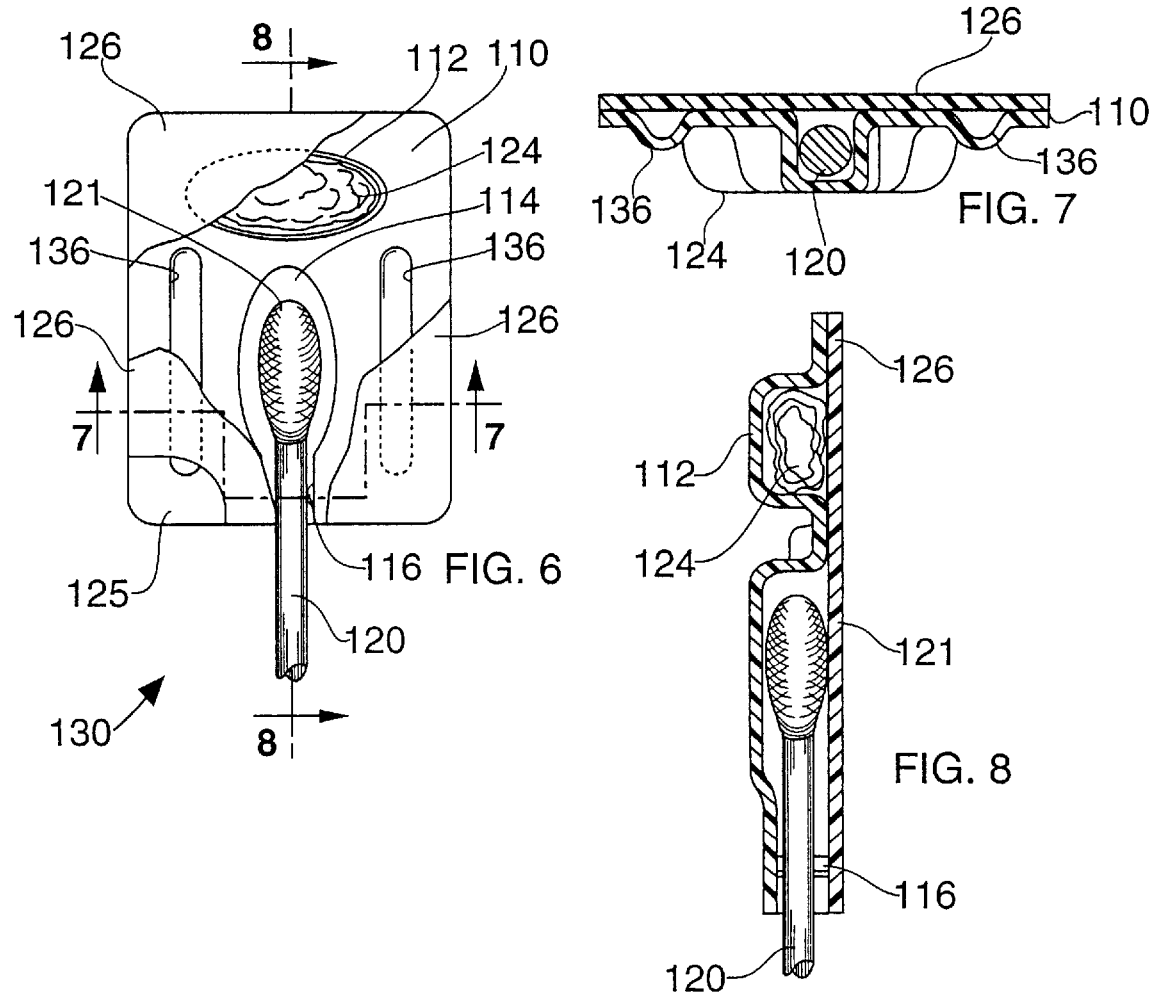
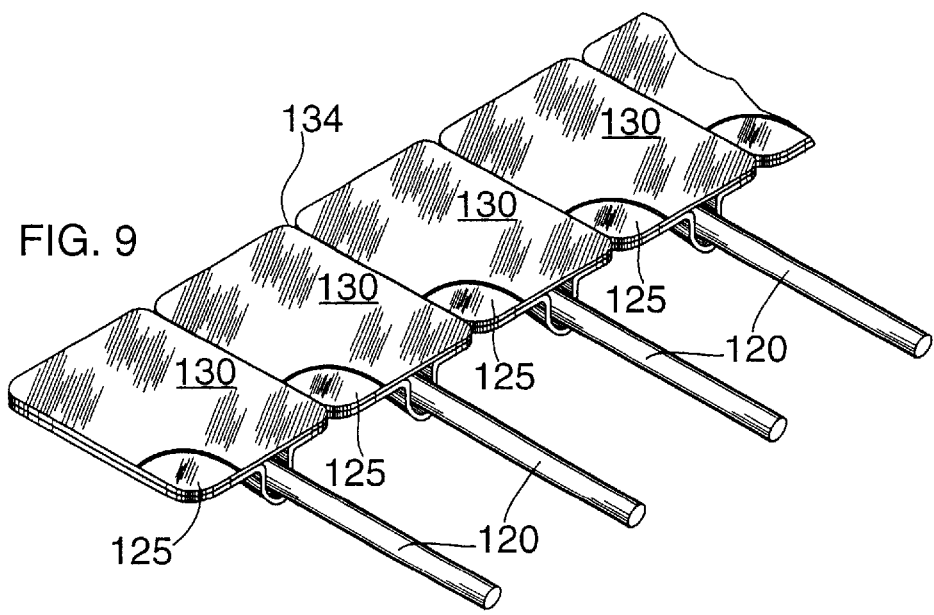

SINGLE PATIENT DOSE MEDICAMENT DISPENSER WITH APPLICATOR

RELATED APPLICATIONS

This application is a divisional of U.S. patent application Ser. No. 08/680,136 filed Jul. 15, 1996, now U.S. Pat. No. 5,954,996 which is a continuation-in-part of U.S. patent application Ser. No. 08/275,003 filed Jul. 13, 1994 and now U.S. Pat. No. 5,660,273.

FIELD OF THE INVENTION

The present invention relates generally to packaging for the dispensing of a medicament to be applied by an applicator, and more particularly to a disposable easy to use single patient dose medicament dispenser or package having an applicator.

BACKGROUND OF THE INVENTION

In many applications, and in particular the medical and dental professions, it is often necessary to apply a small amount of material with an applicator. Often, a dedicated applicator must be associated with the material to be applied. This is a result of the characteristics of the material to be applied or the desire and need to apply the material or a medicament to a single patient and then discarding the remainder to prevent the possibility of cross contamination between multiple patients. Presently in the medical profession, it is common to use a bulk container containing a medicament in combination with a multitude of disposable applicators such as brushes, spatulas, or cotton swabs. While in these applications the applicator is disposed of after each use, the possibility exists for the bulk container to become contaminated and therefore unusable, or if undetected, posing a health risk. Often it is difficult to determine whether or not a bulk container has become contaminated. Additionally, in many instances it is difficult to determine whether an applicator has been used and therefore contaminated. Often, applicators have been purchased and stored separately from the medicament or material to be applied. For example, a single use applicator is disclosed in U.S. Pat. No. 5,001,803 entitled "Disposable Dental Brush" issuing to Discko on Mar. 26, 1991. Therein disclosed is a disposable dental brush for applying various dental materials having an elongated handle with a tuft of bristles at one end. Additionally, various trays for holding and assisting in the dispensing of materials and medicaments are known. One such tray is disclosed in U.S. Pat. No. 5,106,297 entitled "Dental Bond Liquid and Sealant Tray" issuing to Discko on Apr. 21, 1992. Therein disclosed is a dental tray having depressions therein for holding a bottle of dental material and a plurality of distinctive shaped wells used for mixing. The common practice of dispensing a bulk material or medicament onto a tray that is supplied separately and in bulk and mixed with an applicator that is supplied separately and in bulk is often difficult and confusing. Often upon opening a bulk container, it requires some time to locate a tray as well as an applicator. Often one of the components necessary is missing or not readily available. Therefore, the procedure, once started, cannot be completed immediately. This is particularly disadvantageous in the application of materials or medicaments that require a specified amount of time in order to be effective. For example, this is true with materials or medicaments that are light sensitive or that have begun a chemical reaction that once started, cannot be stopped. One such system that has contributed to the ease of use in applying a medicament is disclosed in U.S. Pat. No. 5,240,415 entitled "Dental Bleach System Having Separately Compartmented Fumed Silica and Hydrogen Peroxide and Method of Using" issuing to Haynee on Aug. 31, 1993. Therein disclosed is a supply of fumed silica provided in a mixing chamber and a supply of hydrogen peroxide solution provided in an ampule packaged together with a spatula for mixing and applying the medicament after mixing to a dental surface. While the invention disclosed in this patent contributes to the easy use of medicaments, it constitutes a relatively large packaging system that is often difficult to open and use. Therefore, there is a need for a different packaging concept that will be easier to open and use, less costly to manufacture with less wasted material and provide easy handling.

SUMMARY OF THE INVENTION

The present invention is a single patient dose package for storing, dispensing, and applying a material or medicament that requires an applicator such as a brush, swab, spatula or the like. A tray is formed having a medicament well and an applicator well. The applicator well is configured to prevent contact with the medicament in the medicament well prior to the intended use and application of the medicament in a particular procedure. The applicator well has formed therein a retaining means for holding an applicator in position therein. The applicator well is shorter than the applicator permitting a portion of the applicator to extend beyond the applicator well and one edge of the tray. A cover covers the tray, medicament well, and applicator well preventing contamination of the applicator and the medicament contained within the tray.

Accordingly, it is an object of the present invention to provide a convenient, single patient dose package that is easy to use and open.

It is a further object of the present invention to prevent potential contamination of a medicament and the applicator due to prolonged exposure during storage prior to use.

It is an advantage of the present invention that the single dose package is easy to open.

It is a further advantage of the present invention that the single dose package with applicator requires a minimum amount of packaging material in the making thereof.

It is a feature of the present invention that a portion of the applicator extends beyond the tray and affixed cover.

It is a further feature of the present invention that a disposable applicator is conveniently associated with a single patient dose of medicament in a convenient, easy to use package.

These and other objects, advantages, and features will become readily apparent in view of the following more detailed description.

BRIEF DESCRIPTION OF THE DRAWINGS

FIG. 1 is an exploded perspective view of one embodiment of the invention.

FIG. 2 is an assembled perspective view of the embodiment illustrated in FIG. 1.

FIG. 3 is a cross section taken along line 3—3 in FIG. 2.

FIG. 4 is a cross section taken along line 4—4 in FIG. 2.

FIG. 5 illustrates a top view of a plurality of connected single packages of the embodiment of FIG. 1.

FIG. 6 is a plan view, partially sectioned, illustrating another embodiment of the invention.

FIG. 7 is a cross section taken along line 7—7 in FIG. 6.

FIG. 8 is a cross section taken along line 8—8 in FIG. 6.

FIG. 9 is a perspective top view illustrating a plurality of connected single packages of the embodiment of FIG. 6.

DETAIL DESCRIPTION OF THE PREFERRED EMBODIMENTS

Figure 10:
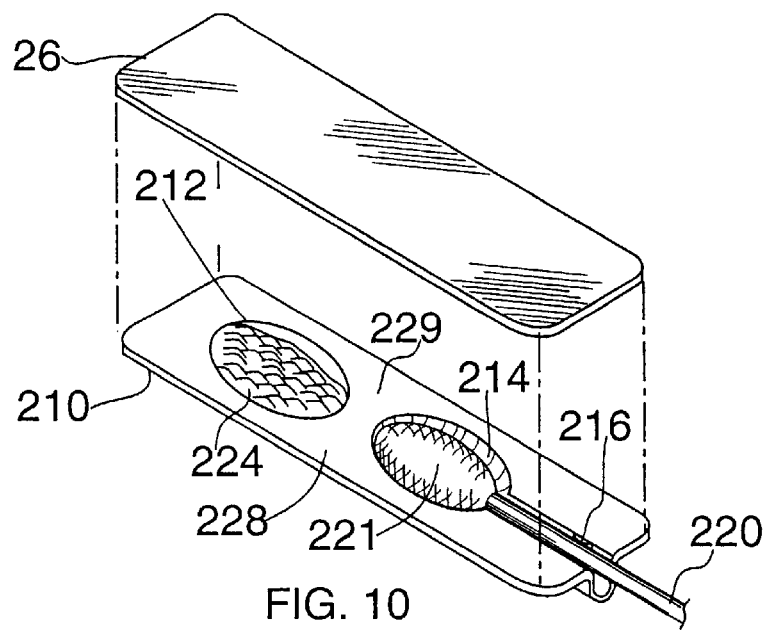
FIG. 10 is an exploded view of another embodiment of the invention.

FIG. 1 illustrates one embodiment of the present invention. A tray 10 has formed therein a material or medicament well 12 and an applicator well 14. Tray 10 may be made from a plastic material that is easily vacuum formed in order to make the medicament well 12 and applicator well 14 therein. Formed within applicator well 14 is a retainer 16 and a seal 18. The retainer 16 and seal 18 are protrusions that extend into the interior of the applicator well 14 a predetermined distance. The applicator well 14 is adapted to receive a portion of an applicator. The applicator may be a spatula, cotton swab, sponge swab or the like. In this embodiment the applicator is illustrated as a brush 20. Brush 20 has a crimp 22 therein, and bristles 21. The brush 20 may be a brush having construction similar to that disclosed in U.S. Pat. No. 5,001,803 entitled "Disposable Dental Brush" issuing to Discko on Mar. 26, 1991, which is herein incorporated by reference. The brush portion of the applicator brush 20 fits within well 14 with the major portion of the brush applicator handle 20A extending beyond the tray 10. The retainer 16 is positioned to contact the crimp 22 on applicator brush 20. This helps to prevent the applicator brush 20 from being unintentionally removed from the applicator well 14. As shown, a substantial portion of the applicator or brush 20 extends beyond the open end or edge of the applicator well 14. However, in some applications only a portion of applicator brush 20 sufficient to grasp easily need extent beyond the open end of the applicator well 14. Seal 18 at the end of applicator well 14 helps to prevent contamination from entering the open end of applicator well 14. A medicament 24 is placed within medicament well 12. The volume of medicament 24 placed within medicament well 12 is a volume that is sufficient to perform a specific procedure for a single patient, and may take into consideration the working time of the material or medicament 24. After insertion of the medicament 24 and the applicator or brush 20 within their respective wells, a cover 26 is affixed to top planar surface 28 of tray 10. The cover is a thin flexible sheet material, preferably made of clear transparent or light opaque plastic material. This may be done with an adhesive or heat sealing. The adhesively affixing or heat sealing of the cover seals the medicament 24, the applicator portion of the brush or applicator within the tray and also helps to hold the applicator or brush 20 within the applicator well 14.

FIG. 2 illustrates the present invention in assembled form. After assembly, a single patient dose or unit dose package 30 is formed. Cover 26 extends over the entire top surface of tray 10. The handle portion of applicator brush 20 extends beyond the open end or edge of applicator well 14, yet is securely held therein. The extension of applicator handle 20A beyond the tray substantially reduces the amount of material normally required in a disposable single patient dose or unit dose type package requiring an applicating device. The applicator or brush 20 also acts as a handle for grasping the entire package. The extension of the applicator or brush 20 beyond the applicator well 14 also helps in removing the cover 26 which is often securely attached to the top surface of tray 10. The applicator handle 20A may be used to pry upward the cover 26. This is a particular advantage in that often during many medical procedures, rubber gloves are required which would otherwise make it extremely difficult to separate the cover 26 from the top surface of tray 10.

FIG. 3 illustrates, in this embodiment, that a continuous seal 32 is formed between the medicament well 12 and the applicator well 14. This assures that the medicament is positively contained in medicament well 12 and does not unintentionally contact applicator or brush 20 until the cover 26 is removed.

FIG. 4 more clearly illustrates the applicator well 14 formed within tray 10. The applicator well 14 has lips 13 that extend inward along the upper longitudinal edges of well 14 between protrusions 16 and 18 to firmly secure the applicator or brush 20 within the applicator well 14. The sides of the applicator well 14 are flexible, therefore permitting the applicator or brush 20 to be pushed through the opening past the lips 13. The distance between lips 13 is less than the diameter of the applicator or brush 20. While FIG. 4 illustrates a gap between cover 26 and the top surface of applicator or brush 20, often the cover 26 material is thin and flexible, and depending upon the sealing process used, the cover 26 may be forced downward contacting the top surface of the applicator or brush 20 further helping to retain the applicator or brush 20 within the applicator well 14 and sealing it from possible contamination. This is often the case when heat sealing is used in combination with a slight vacuum.

FIG. 5 illustrates the present invention in the form of a plurality of single patient dose or unit dose packages 30 formed as a continuous strip or a plurality of connected packages 30 being frangibly connected together by a readily frangible connection 34. The individual single patient dose or unit dose package 30 may be easily snapped off at the frangible connection 34 for use. The feature of the present invention illustrated in FIG. 5 of providing a plurality of frangibly connected single patient dose or unit dose packages 30 is particularly applicable when a particular procedure may require a sequence of applications of the same or different material, in which case the number of applications or different materials for a given procedure is conveniently provided together. Additionally, the portion of the applicator or brush 20 that extends from the tray 10 may be used to correctly identify the sequence of application or material by color of the applicator or brush 20. A different color or shade being used for each different material or application.

FIGS. 6–9 illustrate another embodiment of the present invention. FIG. 6 illustrates a tray 110 having a medicament well 112 and an applicator well 114 formed therein. Within applicator well 114 is a retainer 116. Retainer 116 helps to hold an applicator swab 120. The applicator swab 120 has a cotton swab 121 on one end thereof. In this embodiment the cotton swab 121 contributes to holding the applicator swab 120 within the applicator well 114. The other end of applicator swab 120 extends beyond the open end or edge of applicator well 114. Also formed within the tray 110 are support ribs 136. The support ribs 136 add some rigidity to the tray 110 and permit the use of thinner stock material in forming the tray 110. The ribs 136 reduce the top surface area that is affixed to the cover 126. This helps removal of the cover 125. Medicament 124 is placed in the medicament well 112. A cover 126 covers the entire top surface of tray 110 except for the ribs 136. The cover 126 is typically a thin flexible sheet material as hereinbefore described that may be affixed with adhesive or thermally sealed to the top surface of tray 110. For illustration purposes only, the cover 126 illustrated in FIG. 6 has been sectioned. Typically, the cover 126 covers the entire top planar surface of tray 110, with the exception of exposed portion 125 and depressed ribs 136. The exposed portion 125 facilitates the removal of the cover 126. The tray 110 can be grasped by the exposed portion 125 while the applicator swab 120 is pried upward, facilitating removal of the cover 126. FIGS. 7–8 are cross section views more clearly illustrating the construction of this embodiment. FIG. 9 illustrates a plurality of single patient dose or unit dose packages 130 being connected with a frangible connection 134 as hereinbefore described.

Figure 11:
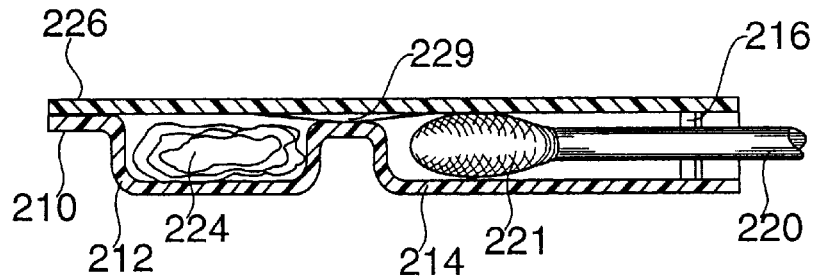
FIG. 11 is a cross section illustrating the embodiment illustrated in FIG. 10.
Figure 12:
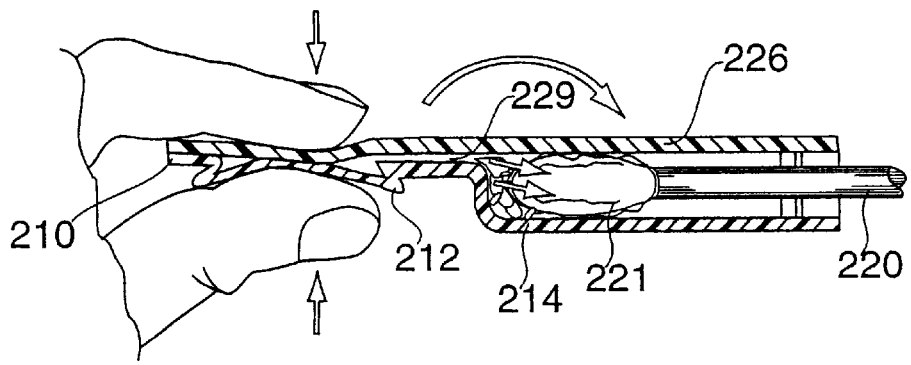
FIG. 12 is a cross section illustrating the embodiment of FIG. 10 in use.

FIGS. 10–12 illustrate another embodiment of the present invention. In this embodiment, tray 210 has a medicament well 212 and an applicator well 214 formed therein. Within applicator well 214 is formed a retainer 216. Retainer 216 also helps to seal the applicator well 214 from external contamination. An applicator swab 220 having a cotton swab 221 on one end thereof is placed within the applicator well 214. A portion of the applicator swab 220 extends beyond the open end or edge of applicator well 214. Placed within medicament well 212 is a medicament 224. Along the top surface of tray 210 is placed an adhesive 228. The adhesive is absent from a portion of the top surface of tray 210 at adhesive free section 229 extending between the respective wells 212 and 214. This adhesive free section forms a channel between the medicament well 212 and the applicator well 214. FIGS. 11 and 12 illustrate a section of the adhesive free section 229. Because there is no adhesive over a small width between the medicament well 212 and the applicator well 214, the medicament well 212 may be squeezed as illustrated in FIG. 12, with the cover 226 in place, forcing the medicament 224 to pass through the adhesive free section 229 and into the applicator well 214 and onto the cotton swab 221 of applicator swab 220. The applicator swab 220 is then removed for applying the medicament.

Figure 13:
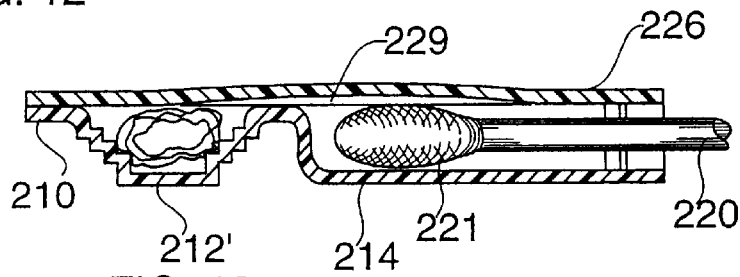
FIG. 13 is a cross section illustrating another embodiment of the invention of the type shown in FIG. 10.

FIG. 13 illustrates a slightly modified embodiment wherein the medicament well 212' has a slightly different structure to that illustrated in FIGS. 10–12. In FIG. 13 the medicament well 212' has a diminishing stepped or bellows structure that facilitates collapsing of the medicament well 212' when squeezed. The step structure is made of a plurality of substantially concentric wells with each adjacent well having a slightly smaller periphery or circumference.

Figure 14:
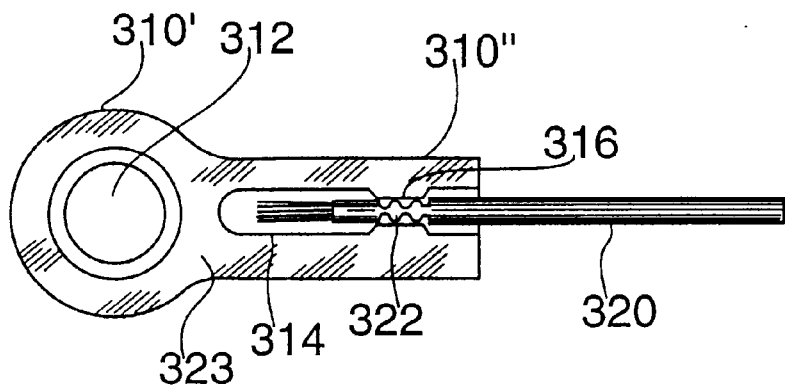
FIG. 14 is a plan view illustrating another embodiment of the invention.
Figure 15:
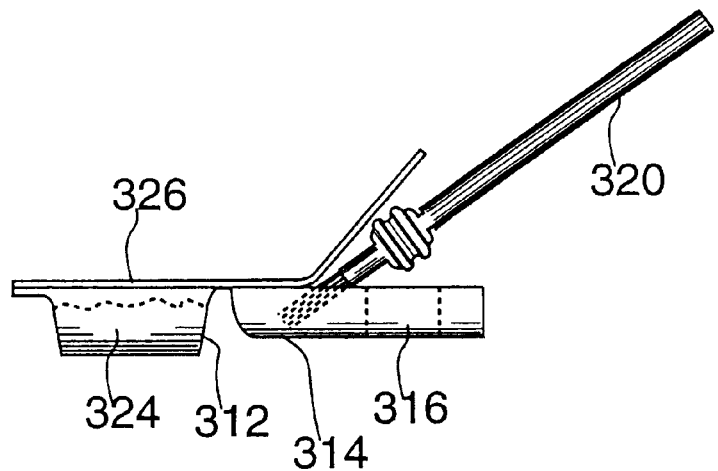
FIG. 15 is a front elevational view illustrating the operation of the embodiment illustrated in FIG. 14.

FIGS. 14–15 illustrate another embodiment of the present invention that further reduces to a minimum packaging material used in a single patient dose or a unit dose package. FIG. 14 illustrates a round head portion 310' having a rectangular tail portion 310". The round head portion 310' has a round medicament well 312 therein. The rectangular tail portion 310" has an applicator well 314 formed therein. The applicator well 314 has a retainer portion 316 that extends inwardly within the applicator well 314. The retainer portion 316 also helps to seal the applicator well 314 from external contamination. The retainer portion 316 corresponds to a crimp 322 formed on the applicator or brush 320. A substantial portion, greater than one-half of the length, of the applicator or brush 320 extends beyond the open end or edge of the applicator well 314. Therefore, only a minimum amount of material is required in the package. The top surface 323 of the round head portion 310' and the rectangular tail portion 310" forms a sealing surface.

Figure 14A:
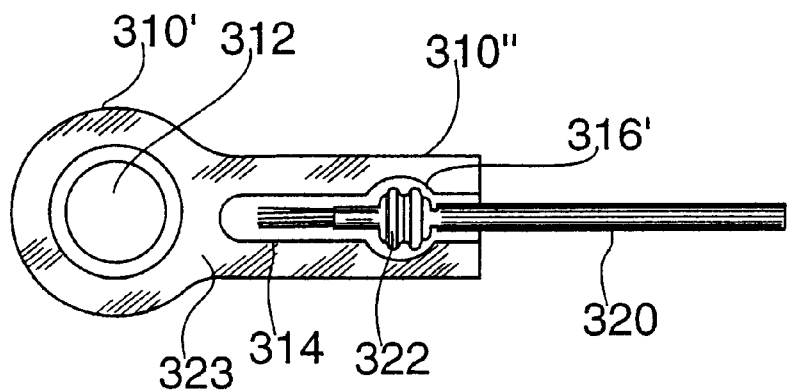
FIG. 14A is a plan view illustrating another embodiment of the invention.

FIG. 14A illustrates another embodiment of the present invention. This embodiment is similar to the embodiment illustrated in FIG. 14, with the exception that the retainer 316' extends outwardly rather than inwardly. The outward shape of the retainer 316' matches that of the broad exterior periphery of the crimp 322 when the brush 320 is rotated 90°. The broad exterior periphery of the applicator brush crimp 322 on the applicator brush 320 is wider than the lateral width of the applicator well 314. Therefore, the applicator brush 320 is securely held within the applicator well 314 and cannot be easily pulled out of the applicator well 313 after a cover is affixed to the planer surface 323. The enlarged retainer 316 facilitates placement of the applicator brush 320 within the applicator well 314 in the assembly of the package. This embodiment permits placement of the applicator brush 320 within the applicator well 314 at substantially any angular rotation along the longitudinal axis of the applicator brush 320.

Referring to FIG. 15, a cover 326 is applied to the top surface 323. The cover 326 is typically made of a thin flexible sheet material that seals along the entire top surface 323 as hereinbefore described. As illustrated in FIG. 15, the portion of the applicator brush 320 extending beyond the open end or edge of the applicator well 314 is easily held and used to pry up a portion of the cover 326, facilitating easy removal thereof when desired. This easy cover removal feature of the present invention is of great advantage, especially in many medical applications when rubber gloves are used, which would otherwise render it very difficult to separate the cover 326 from the planar surface 323. Upon removal of the cover, the medicament 324 may be easily and conveniently applied whereupon the entire package and applicator can be readily disposed of after use.

Figure 16:
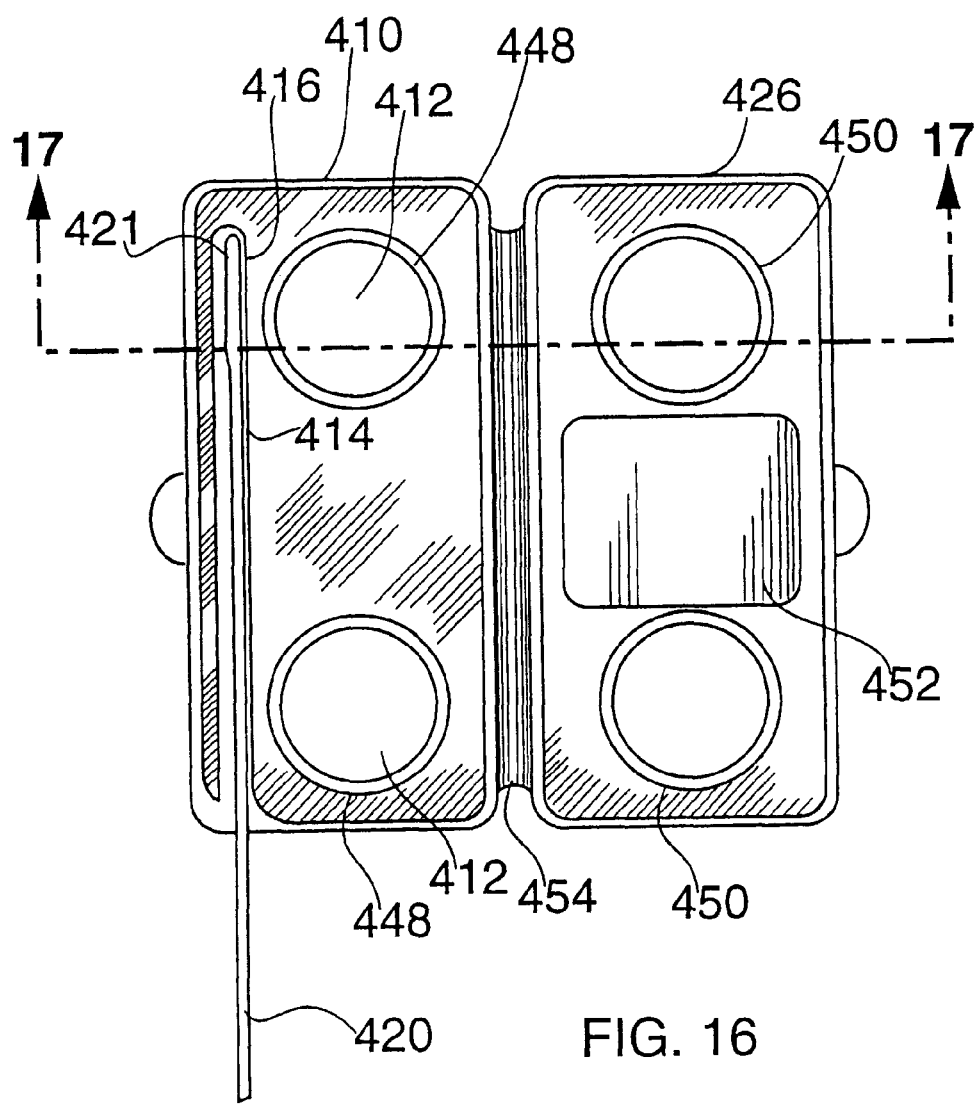
FIG. 16 is a plan view of another embodiment of the invention.
Figure 17:
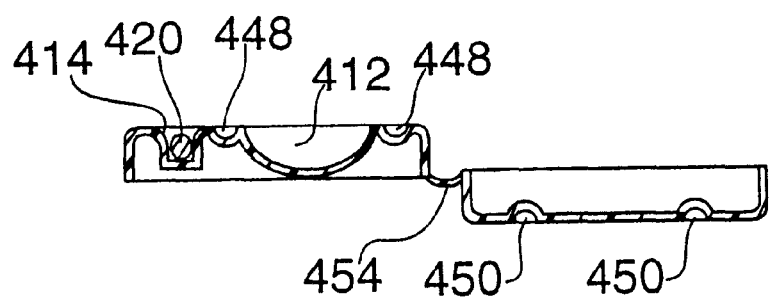
FIG. 17 is a cross sectional view of the embodiment illustrated in FIG. 16 taken along line 17—17.

FIGS. 16–17 illustrate another embodiment of the present invention. This embodiment is particularly applicable to procedures requiring the mixing of two or more materials in a particular procedure. Many procedures require the mixing of two materials that chemically interact. In this form, the tray 410 has formed therein at least two medicament wells 412 and an applicator well 414. Within applicator well 414 is a suitable applicating device, e.g. a spatula applicator 420. Spatula applicator 420 has a broad flat portion 421. The broad flat portion 421 has a dimension greater than the diameter of the handle portion of spatula applicator 420. A closed end portion 416 of the applicator well 414 has a depth that is greater than the depth of the portion of the remaining length of the applicator well 414 that receives the handle portion of the spatula. The broader spatula portion 421 of the spatula applicator 420 fits within this deeper closed end portion 416 and forms a means for retaining the spatula applicator 420 within the package or tray 410. Also formed within tray 410 circumscribing the medicament wells 412 are female sealing rings or grooves 448. The tray 410 is provided with a hinged cover 426. The cover 426 is attached with an integral flexible living hinge or web 454. Formed within cover 426 are male or projecting sealing rings 450. Male sealing rings 450 in the closed position of the hinged cover 426 are arranged to mate and interlock with female sealing rings or grooves 448. Also placed on cover 426 is a mixing area 452. The mixing area 452 may optionally be placed on the tray portion 410 between the medicament wells 412.

Figure 18:
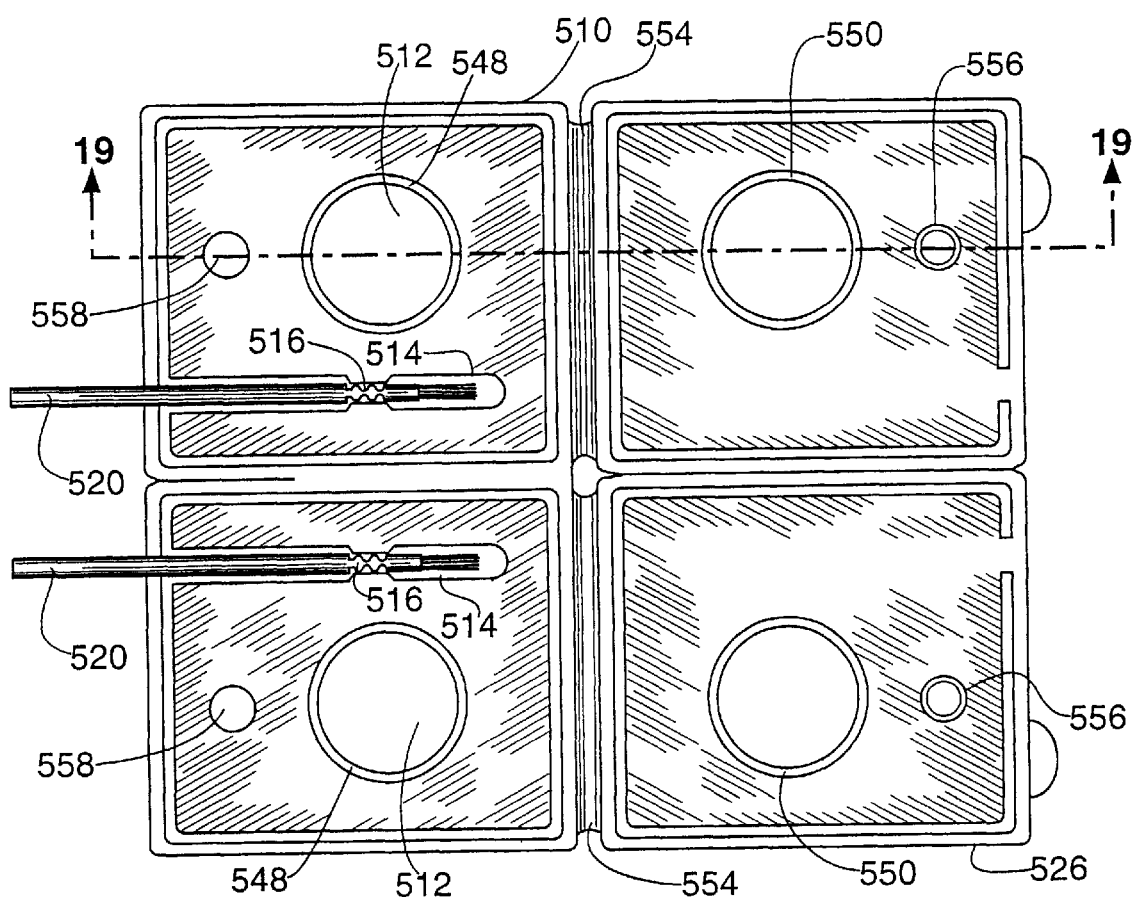
FIG. 18 is a plan view of another embodiment of the invention.
Figure 19:
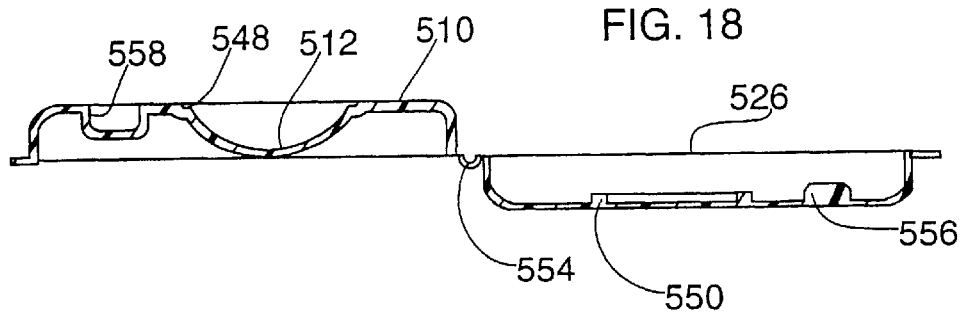
FIG. 19 is a cross sectional view of the embodiment illustrated in FIG. 18 taken along line 19—19.
Figure 20:
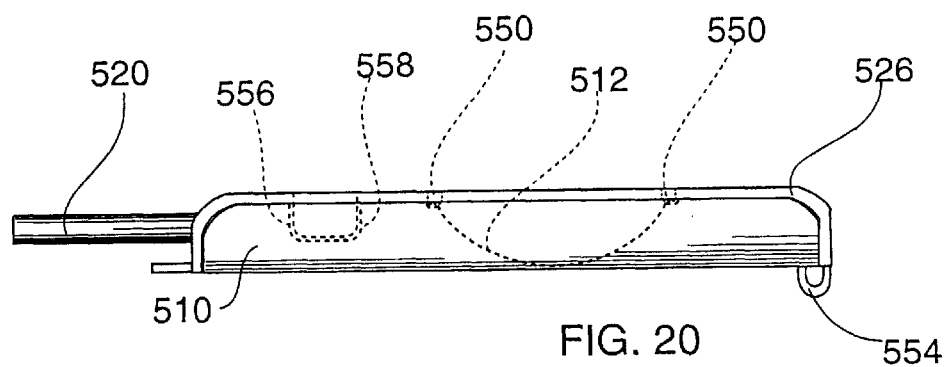
FIG. 20 illustrates the side view of the embodiment of FIG. 18 in the closed or assembled position.

FIGS. 18–20 illustrate another embodiment of the present invention. A tray 510 has formed therein at least two medicament wells 512 and at least two applicator wells 514. Each of the medicament wells 512 have a female sealing ring or groove 548 circumscribing it. Formed within each of the applicator wells 514 is a retainer 516. Retainer 516 protrudes into the applicator well 514 for holding an applicator or brush 520 therein. The retainer, although not illustrated, may also be wider than the width of the applicator well 514 as described for the embodiment shown in FIG. 14A. Adjacent each medicament well 512 is a female locking tab 558. Covers 526 are attached to the tray 510 by integral hinge or web 554. Each of the covers 526 may be opened and closed independently. Formed within each cover 526 is a male sealing ring 550 for sealing its corresponding medicament well in the closed position. The male sealing rings or projection 550 are adapted to mate with corresponding female sealing rings or grooves 548 formed within the tray 510 in the closed position. Associated with each cover 526 is a male locking tab 556. Male locking tabs 556 of the cover 526 are adapted to mate with female locking tabs 558 of the tray in the closed position. This embodiment of the present invention is particularly applicable to a procedure requiring a two part application of a medicament. In this embodiment, an applicator brush 520 is associated with each of the medicament wells 512. Additionally, some of the medicaments may be light sensitive and need to be applied sequentially. This embodiment provides for covers 526 that can be independently opened and closed as may be needed to permit application of the medicament for one part of the procedure without opening or uncovering the medicament required for a second part of a procedure.

Figure 21:
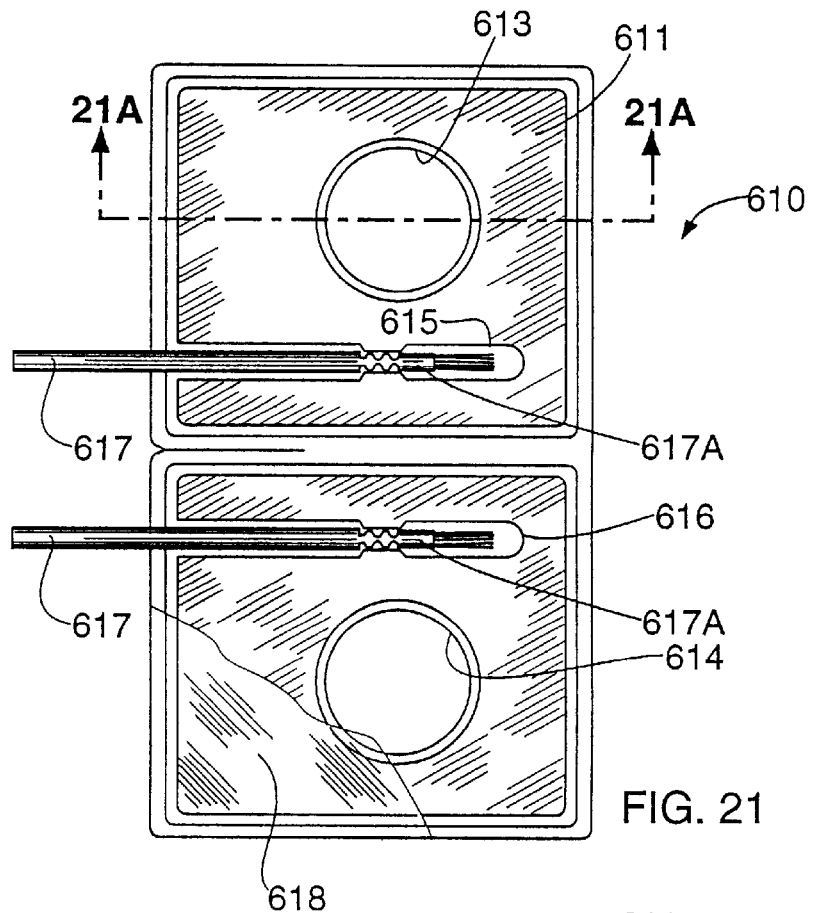
FIG. 21 is a plan view of another embodiment of the invention.
Figure 21A:
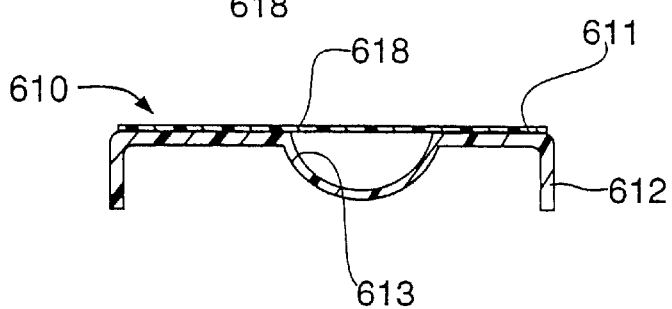
FIG. 21A is a sectional view taken on line 21A—21A on FIG. 21.

FIGS. 21 and 21A illustrate a further embodiment of the invention. In this form, the tray 610 is vacuum formed from a sheet of plastic which is formed with a top or plane surface 611 about which there is formed a circumscribing depending side wall 612. In this form of the invention, the top or plane surface 611 is provided with at least two depressions to define spaced apart wells 613 and 614 which are adapted to receive a suitable medicament or dental material. Frequently in a medical or dental application or procedure, a two part medicament or material is required. For example, in dentistry, many chemically cured materials are used to perform various dental procedures which must be kept separated until readied for use. The tray dispenser of FIG. 21 is particularly applicable for unit dispensing such materials. Each such material is placed in each of the wells 613 and 614. The amount of material placed in wells 613 and 614 is sufficient to formulate a unit or single dose. Also formed in the top or plane surface 611 is an elongated recess 615 and 616 arranged to receive a suitable applicator 617, e.g. a brush, spatula and the like, as previously described with respect to FIG. 18. In this form of the invention, a plastic film 618 is adhesively secured to the top plane of the tray to protect and cover the top plane including the wells 613, 614 and the material contained therein and the elongated recess containing the applicating head or end 617A of the respective applicator 617. It will be understood that the covering film 618 may be rendered transparent or light opaque, depending upon the nature and/or characteristics of the material contained in the wells 613, 614. To use the tray dispenser 610 of FIGS. 21, 21A, the user need only to remove the covering film 618 to expose the material in the wells and the associated applicator.

Figure 22:
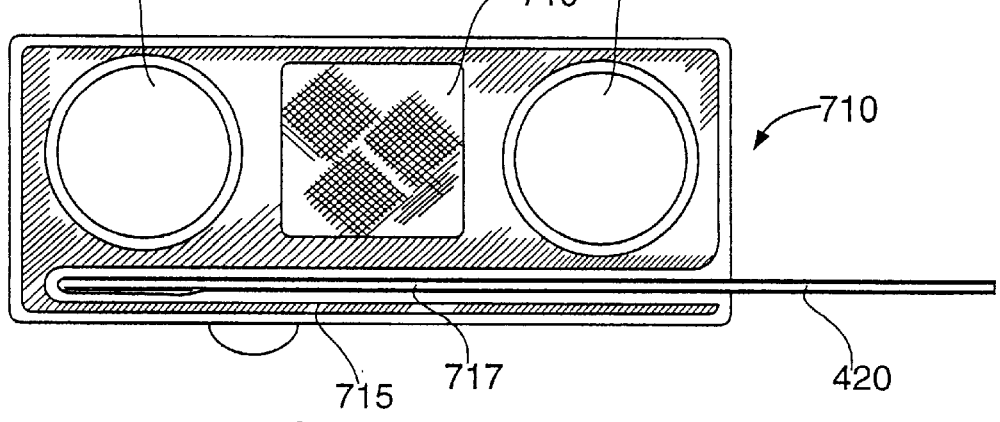
FIG. 22 is a plan view of still another embodiment of the invention.

FIG. 22 is directed to a modified form of the dispenser tray shown in FIG. 21. In this form, the dispenser tray 710 is also in vacuum form similar to that of FIG. 21, except that it may be made somewhat smaller since only one applicator 717 is required. Between wells 713 and 714, there is formed a mixing area 719. If desired, the mixing area 719 may be provided with a serrated or roughened surface. The applicator 717 is stowed in an elongated recess 715 extending along the length of the tray 710. With the material placed in the wells and the applicator 717 in place, the tray 710 is covered with a plastic film or sheet and adhesively secured thereto as hereinbefore described.

Figure 23:
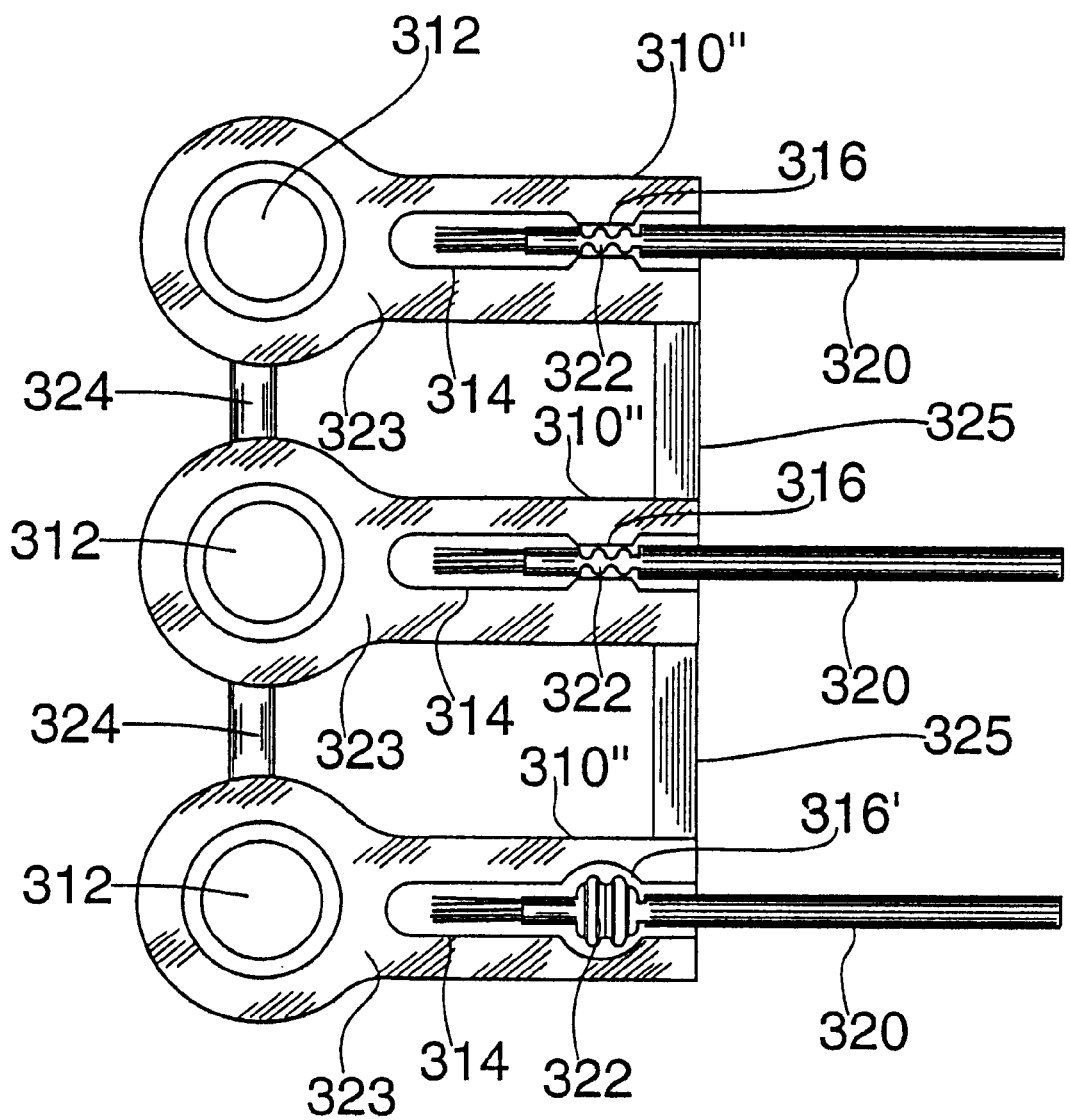
FIG. 23 is a plan view of another embodiment of the invention.

FIG. 23 illustrates a dispenser tray as described with respect to FIGS. 14 or 15 wherein the dispenser trays are integrally connected by a front web 324 and a rear web 325. It will be understood that the webs 324 and 325 are provided with a frangible portion to facilitate separating one tray from the other. In this form, the individual trays are chain connected by webs 324 and 325 permitting the trays to be sold in clusters or groups.

Figure 24:
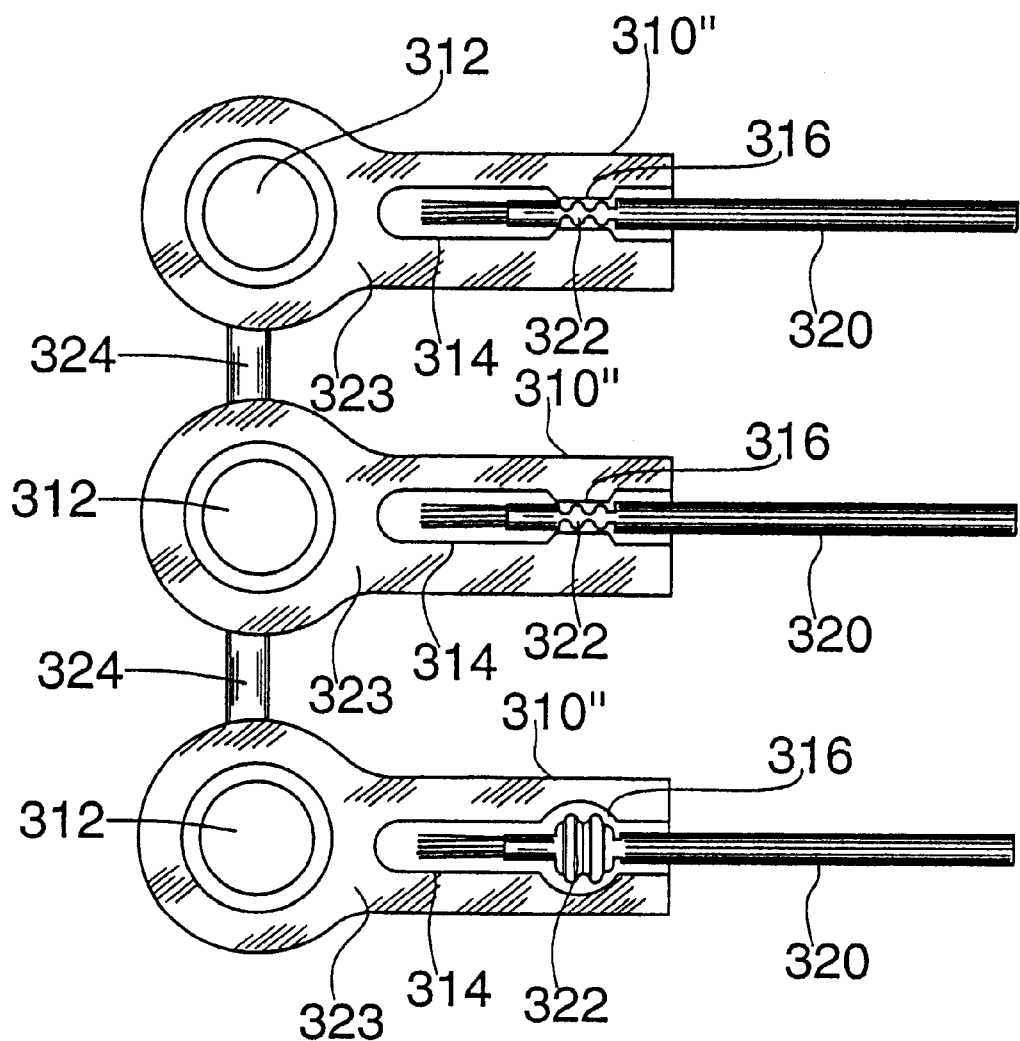
FIG. 24 is a plan view of another embodiment of the invention.

FIG. 24 illustrates the trays as described in FIG. 14 or FIG. 14A integrally connected only by a single web 324.

Figure 25:
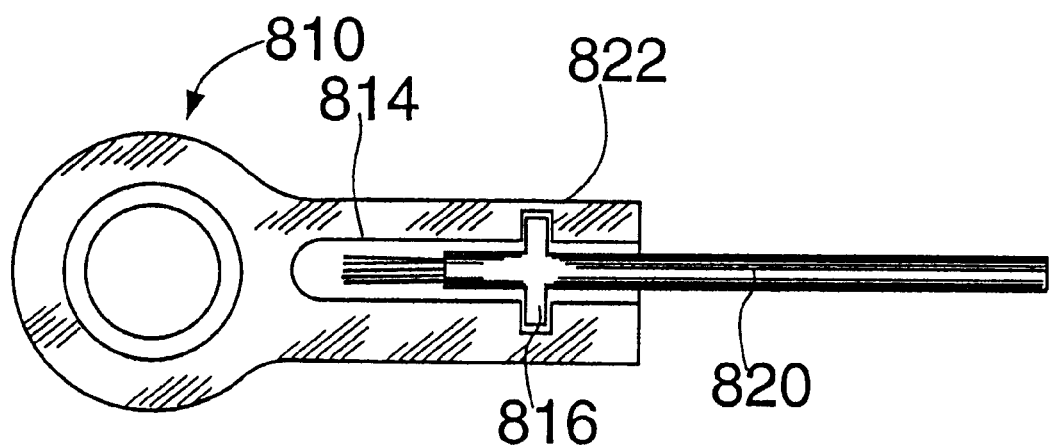
FIG. 25 is a plan view of still another embodiment of the invention.

FIG. 25 illustrates a further embodiment of the invention. This form of the invention is similar to that described with respect to FIGS. 14, 14A, or 15 wherein the applicator 820 has been modified to include a flange 822. The recess or applicator well 814 is also modified to provide a recess portion 816 to accommodate the flange 822 of the applicator 820. The arrangement is such that the flange 822 prohibits the applicator 820 from being accidentally or inadvertently pulled out of the dispenser tray 810. In all other respects, the dispenser tray of FIG. 25 is similar to that hereinbefore described.

Accordingly, it should readily be appreciated that the present invention, in providing a single patient dose or a unit dose package that is easy to use and open having a dedicated applicator associated with each medicament clearly facilitates the ease of applying small quantities of material safely and conveniently.

The invention has been particularly described for use as a single dose medicament package with a dedicated applicator so as to be readily disposable after use. However, it will be understood that the invention may also have non-medical or industrial uses. Also, the package described can be used as a sampler for allowing consumers to test or try various types of products. It will also be understood that the medicament can be a liquid, gel or powder or any combination thereof.

The medicament may also be a dental etch or etchant such as that disclosed in U.S. application Ser. No. 08/680,136 filed Jul. 15, 1996, entitled "Dental Etch and Package Therefor", which is herein incorporated by reference.

While the present invention has been described with respect to various embodiments, various modifications may be made without departing from the spirit and scope of this invention.

What is claimed:

1. A single dose disposable dispenser for dispensing a material comprising:
    a tray having at least two wells formed therein, one of said wells for receiving and containing a material to be dispensed and the other well adjacent thereto for containing an applicator,
    a cover member connected to said tray sealing the material and applicator within their respective wells,
    said applicator having an applicating end portion and a connected handle portion,
    said applicating end portion being disposed in said applicator well,
    said applicator well having an opening therein through which the handle portion of the applicator extends outwardly of said application well,
    said material well being squeezable so that the material in said material well, when squeezed, is expressed out of said material well and into said adjacent applicator well of said applicator and onto said applicating end portion with said cover member in place.

2. A package as in claim 1 further comprising:
    said material is a dental echant.

3. A single dose disposable dispenser for dispensing a material comprising:
    a tray having at least two wells formed therein, one of said wells being a material well for receiving and containing a material to be dispensed and another well adjacent thereto being an applicator well,
    an applicator having an applicating end portion and a connected elongated handle portion,
    said applicating end portion being disposed in said applicator well,
    said applicator well having an opening therein through which said elongated handle portion of said applicator extends outwardly of said applicator well,
    a cover member connected to said tray for sealing the material and said applicating end portion within their respective wells,
    means adjacent said opening for releasably retaining said applicator relative to said applicator well,
    and said material well being squeezable so that when squeezed, the material in said material is expressed out of said material well and into the adjacent applicator well and onto said applicator end portion with said cover member in place.

4. A single dose disposable dispenser as defined in claim 3 wherein:
    said applicator well includes opposed side walls,
    said opposed side walls being spaced a distance slightly greater than the width of said handle portion,
    said means for releasably retaining said applicator relative to said applicator well, including opposed projections extending inwardly of said applicator well side walls adjacent said opening for frictionally retaining said handle portion therebetween by a force sufficient to prohibit unintentional separation of said applicator from its well.

5. A single dose dispensable dispenser as defined in claim 3 and including:
    said applicator well having spaced apart opposed sidewalls,
    said sidewalls each having an opposed projection extending toward each other,
    and said applicator handle having a reduced portion for receiving said opposed projections when said applicator is placed in said applicator well to prohibit unintentional axial separation of the applicator relative to said applicator well.

6. A single dose dispenser as defined in claim 5 wherein said reduced portion forms a hinge connection between said applicator handle and said applicating end portion.

7. A single dose disposable dispenser as defined in claim 1 and including retainer means adjacent said opening for releasably securing said applicator within said applicator well so as to prohibit any unintentional separation of said applicator from said applicator well.

8. A single dose disposable dispenser as defined in claim 1 and having retainer means defined as opposed projections extending inwardly of said applicator well,
    and said applicator handle portion having complementary indented portions complimenting said opposed projections whereby said opposed projections interlock with said indented portions when said applicator is disposed in said applicator well to prohibit any unintentional separation of said applicator from said applicator well.

9. A single dose disposable dispenser as defined in claim 1 wherein said material well having a collapsible wall portion to facilitate squeezing of the material out of said material well and into said applicator well.

10. A single disposable dispenser as defined in claim 1 and including frangible means for detachably connecting a plurality of said dispensers one to another.

11. A single dose disposable dispenser for dispensing a dental material comprising:
    a tray formed of a sheet material having at least two wells formed therein,
    one of said wells defining a material well for receiving and containing a dental material therein,
    another well adjacent to said material well to define an applicator well,
    an applicator having an elongated handle having a free end and a connected applicating end portion connected to said handle opposite said free end,
    said applicator well having a first portion for receiving said applicating end portion and a connected second portion for receiving a portion of said handle adjacent said applicating end portion,
    said second portion of said applicator well terminating in an opening through which said free end of said handle extends,
    said handle having a reduced portion adjacent said applicating end portion, said reduced portion hingedly connecting said applicating end portion to said handle, whereby said applicating end portion may be disposed at an angle relative to said handle, a cover member connected to said tray to seal said dental material and applicating end portion within their respective wells, means for releasably securing said applicator within said applicator well with a force sufficient to prohibit unintentional separation of said applicator from said applicator well, and means defining a passageway between said material well and said applicator well whereby said material in said material well can be expressed out of said material well and into said applicator well and onto said applicating end portion of said applicator when the material well is squeezed with the cover member in place.

* * * * *